(12) United States Patent
Deckard et al.

(10) Patent No.: US 12,161,604 B2
(45) Date of Patent: *Dec. 10, 2024

(54) QUICK RELEASE CONNECTION FOR PATIENT TUBE ASSEMBLY

(71) Applicant: Wealth Acquisition Group LLC, Arlington, TX (US)

(72) Inventors: Michael R. Deckard, Abilene, TX (US); Henry James Johnson, Jr., Cedar Hill, TX (US); John Cowan, Richardson, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 18/203,091

(22) Filed: May 30, 2023

(65) Prior Publication Data

US 2024/0115464 A1  Apr. 11, 2024

Related U.S. Application Data

(63) Continuation of application No. 16/995,025, filed on Aug. 17, 2020, now Pat. No. 11,701,303.

(51) Int. Cl.
*A61J 15/00* (2006.01)

(52) U.S. Cl.
CPC ....... *A61J 15/0026* (2013.01); *A61J 15/0015* (2013.01)

(58) Field of Classification Search
CPC .............. A61J 15/0026; A61J 15/0015; A61M 39/1011; A61M 2039/1016; A61M 2039/1027
See application file for complete search history.

(56) References Cited

U.S. PATENT DOCUMENTS

| 5,933,556 A * | 8/1999 | Hawkins ............. | F16L 37/0985 385/56 |
| 7,758,085 B2 * | 7/2010 | Guest .................. | F16L 37/0927 285/322 |
| 8,025,318 B1 * | 9/2011 | Morroney ........... | F16L 37/0927 285/322 |
| 2017/0014616 A1 * | 1/2017 | Davis .................... | A61M 39/10 |

* cited by examiner

*Primary Examiner* — Phillip A Gray
(74) *Attorney, Agent, or Firm* — Mark D. Perdue (57) ABSTRACT

An enteral feeding tubing connector comprises a body, a bore extending through the body, and a collet slidably disposed in the bore at a first end of the body. The collet is dimensioned to receive and engage a portion of tubing inserted into the collet, and is configured to resist withdrawal of the tubing from the bore and body upon application of force to the tubing that moves the collet out of the bore. A lock is provided on the first end of the body, and is configured to selectively engage the collet and prevent movement of the collet outward relative to the body. A tubing connection is provided at a second, opposite end of the body, the tubing connection providing fluid communication between another portion of tubing, the bore extending through the body, and the portion of tubing inserted into the collet.

20 Claims, 6 Drawing Sheets

QUICK RELEASE CONNECTION FOR PATIENT TUBE ASSEMBLY

BACKGROUND OF THE INVENTION

1. Field of the Invention

The present invention relates broadly to the field of enteral feeding apparatus. More particularly, the present invention relates to connections for connecting a tube extending from a nutrient container to a feeding tube that enters the body of a patient.

2. Summary of the Prior Art

Enteral feeding, in the medical sense, means feeding of nutrients directly to the stomach (or the small intestine) of a patient through a tube. This can be useful when the patient's mouth, throat, or esophagus is damaged by accident, disease, or surgery, or when a neurological or other problem makes conventional eating difficult or impossible. While "enteral feeding" is a term that describes delivery of nutrients to either the stomach or the intestine, apparatus that enters the stomach is typically referred to as "gastric," while that that enters the intestine is typically referred to as "enteric."

The feeding tube may be a nasogastric (nasoenteric) tube that enters the stomach (intestine) through the nasal passage and esophagus, an orogastric (oroenteric) tube that enters through the mouth and esophagus, or a gastrostomy (jejunostomy) tube that enters the stomach (intestine) through the abdominal wall. All of these tubes may be generally referred to as "feeding tubes" and connect a container of nutrient solution through another, longer, tube commonly referred to as an extension or infusion tube, to the stomach or intestine for delivery of a nutrient solution to the patient.

Particularly in the case of gastrostomy and jejunostomy tubes, which require surgical placement, it is undesirable to have excessive strain exerted on the tube, i.e. to have it "pulled on." In some cases, it merely causes discomfort, in others, it can dislodge or damage the tube or injure the patient, which may require surgical repair and be quite painful to the patient and also pose a risk of infection.

Excessive strain on a feeding tube can come from a variety of sources. Some patients are sedated or somnolent and may move in their sleep in such a way as to exert strain on a tube. Patients, particularly the elderly, can be or become agitated and pull on the tube, either directly or as a result of other movements. Occasionally, movement of medical personnel around a patient can inadvertently exert stress on the feeding tube, as when the personnel trips on, or otherwise becomes entangled with the infusion tube.

A variety of connectors may be used in making up a "feeding set" for enteral feeding. The EnFit® connector standard is designed to provide a connection for feeding tubes that prevents inadvertent "cross-connection" to catheters, IV tubes, and other apparatus. "J-ports" were commonly used to connect tubing before EnFit®. However, none of these connectors is designed to disconnect from the feeding tube entering the body upon application of sufficient strain, that is, to "quick-disconnect" or "breakaway" to avoid injury or discomfort to the patient.

A need exists, therefore, for improvements in enteral feeding sets or systems or apparatus that avoid these problems.

SUMMARY OF THE INVENTION

It is a general object of the present invention to provide an improved connector for enteral feeding sets or systems.

This and other objects of the present invention are achieved by a connector comprising:

a body, a bore extending through the body, and a collet slidably disposed in the bore at a first end of the body. The collet is dimensioned to receive and engage a portion of tubing inserted into the collet, and is configured to resist withdrawal of the tubing from the bore and body upon application of force to the tubing that moves the collet out of the bore. A lock is provided on the first end of the body, and is configured to selectively engage the collet and prevent movement of the collet outward relative to the body. A tubing connection is provided at a second, opposite end of the body, the tubing connection providing fluid communication between another portion of tubing, the bore extending through the body, and the portion of tubing inserted into the collet.

According to one embodiment of the present invention, an elastomer o-ring seal is disposed in the bore adjacent the first end of the body, the o-ring dimensioned to engage and exert force on an exterior of the tubing upon insertion into the end of the body.

According to another embodiment of the present invention, a portion of a feeding tube is received in the first end of the body, and a portion of an extension tube leading to the container of feeding solution is connected by the tubing connection to the other end of the body.

According to yet another embodiment of the present invention, each collet has an exterior surface that tapers along a length of the collet from a larger diameter to a smaller diameter.

According to still another embodiment of the present invention, at least one internal projection is formed on an interior surface of the collet.

According to one embodiment of the present invention, the tubing connection is an EnFit connector.

According to another embodiment of the present invention, the tubing connection further comprises a second collet slidably disposed in the bore at the second end of the body. The collet dimensioned to receive and engage a portion of tubing inserted into the collet, and is configured to resist withdrawal of the tubing from the bore and body upon application of force to the tubing that moves the collet out of the bore. A second lock is provided on the second end of the body, the lock configured to engage the collet and prevent movement of the collet outward relative to the body.

Other objects, features, and advantages of the present invention will become apparent with reference to the drawings and to the detailed description of the invention, which follows.

DETAILED DESCRIPTION

Figure 1:
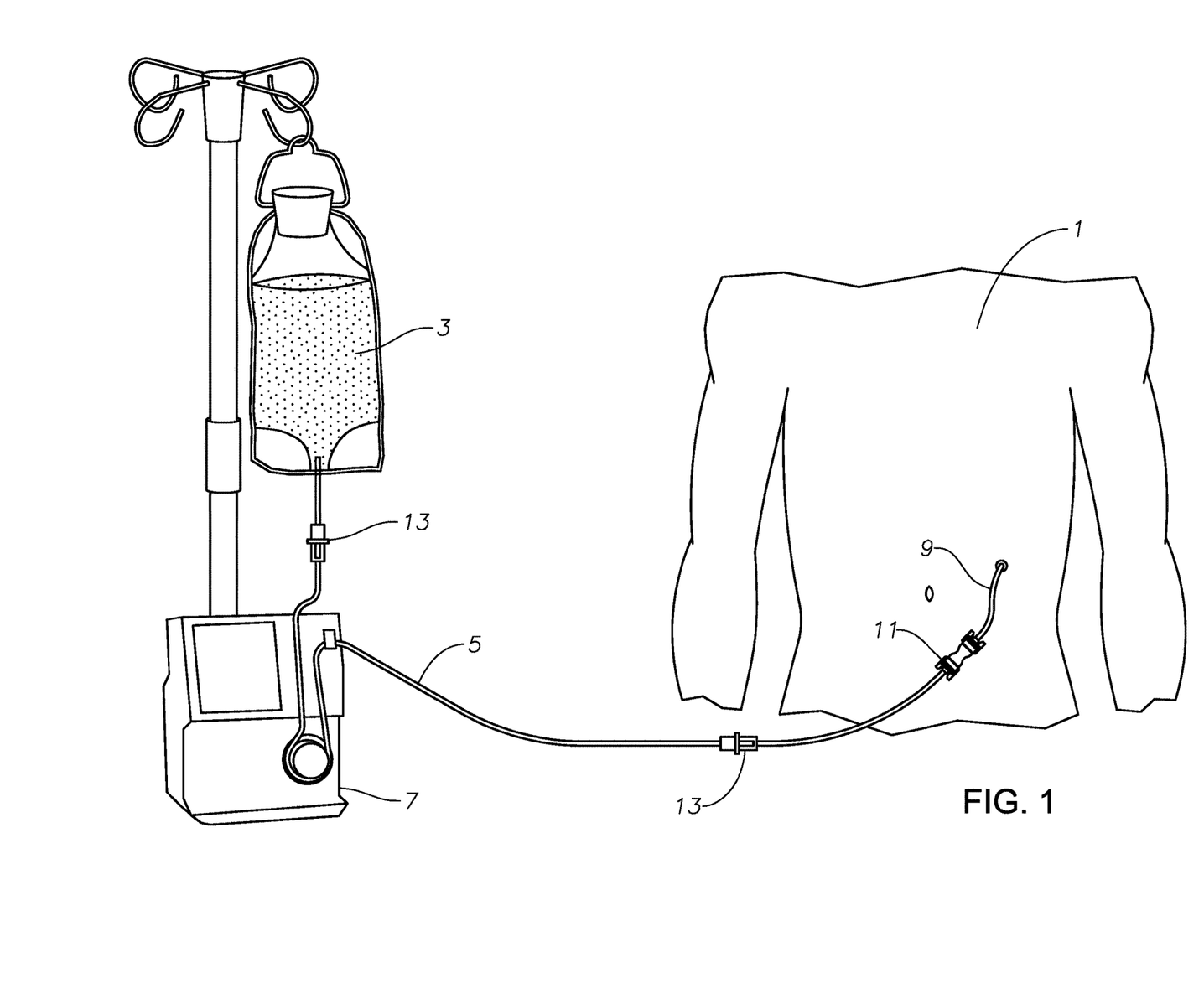
FIG. 1 depicts a patient connected to an exemplary enteral feeding apparatus including a connector in accordance with an embodiment of the present invention.

Turning now to the Figures, and particularly to FIG. 1, an enteral feeding patient 1 is depicted connected to an exemplary enteral feeding arrangement or "feeding set." The enteral feeding arrangement may comprise a container or "bag" 3 of nutrient solution, which is coupled to an infusion or extension tube 5. Nutrient fluid may be gravity-fed or an enteral feeding pump 7 may be connected or coupled to extension tube 5 to provide pressure to the nutrient fluid in the tube. A connector or coupling 11 in accordance with the present invention may be placed between feeding tube 9 and extension tube 5 to provide the "breakaway" or "quick-disconnect" functionality described herein. Other or additional connectors 13 may be provided to connect extension tube 5 to container 3, and another connector 13 closer to feeding tube 9. Feeding tube 9 is illustrated as a gastrostomy tube, but as indicated above, may include any of the various gastric or enteric enteral feeding devices.

According to current practice, connectors 13 preferably may be EnFit® connectors. EnFit® is a trademark of Global Enteral Device Supplier Association, Inc. (GEDSA), 692 N. High St., Suite 304, Columbus, Ohio 43215 and designates a type of connector specifically adapted for enteral feeding connections that is designed to avoid "cross-connection" with other types of fluid connectors, such as catheters or IV lines. It is intended that main or principal connections, which are to be frequently connected or disconnected (as to change nutrient containers or extension tubes), be EnFit® type or compliant connectors.

Figure 2:
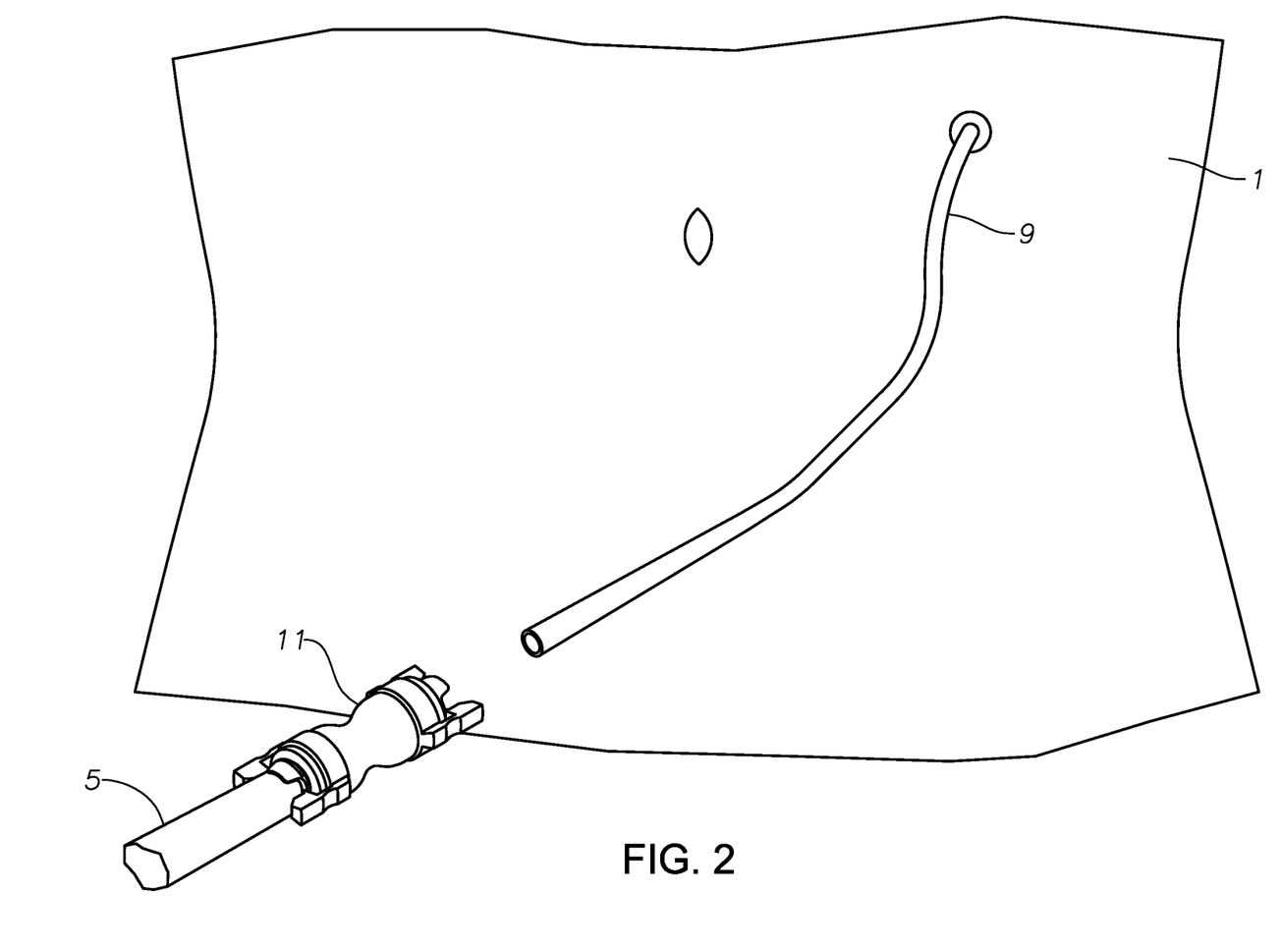
FIG. 2 is an enlarged view of the patient of FIG. 1.

Broadly speaking, connector 11 in accordance with the present invention provides a "breakaway" or "quick-disconnect" function to prevent extension tube 5 from exerting excessive stress or strain on feeding tube 9. As shown in FIG. 2, in the event excessive strain is placed on feeding tube 9 by extension tube 5, connector 11 will disconnect or break away from feeding tube 9 to avoid injury to patient 1 or damage to feeding tube 9. Feeding tube 9 may be a gastrostomy tube, as illustrated, a jejunostomy tube, an orogastric tube, or a nasogastric tube, as discussed above and including intestinal (enteric) feeding tubes in addition to stomach (gastric) tubes. Thus, the term "feeding tube" may encompass any of these.

In contrast to other connectors 13 in the feeding set, connector 11 is not intended to be a main or principal connection that is frequently connected or disconnected. It is intended to be assembled and set in its location between extension tube 5 and feeding tube 9, as illustrated and described herein, and "left alone" until its purpose has been served or reconfiguration or replacement is required. Further, connector 11 connects "bare" tubing rather than to another mating connector. Thus, risk of cross-connection is minimized.

Referring to FIGS. 3 through 6, connector 11 according to a preferred embodiment of the present invention is depicted in an exploded and two longitudinal section views. Connector 11 comprises a body 21, which may be molded or otherwise formed from a polymer material. A bore 23 (FIGS. 4 and 5) extends longitudinally through body 21 and defines an opening at each end. A pair of generally opposing, flexible lock tabs 25 may be provided at each end of body 21 and are biased or sprung toward each other or the central axis of body 21.

Figure 3:
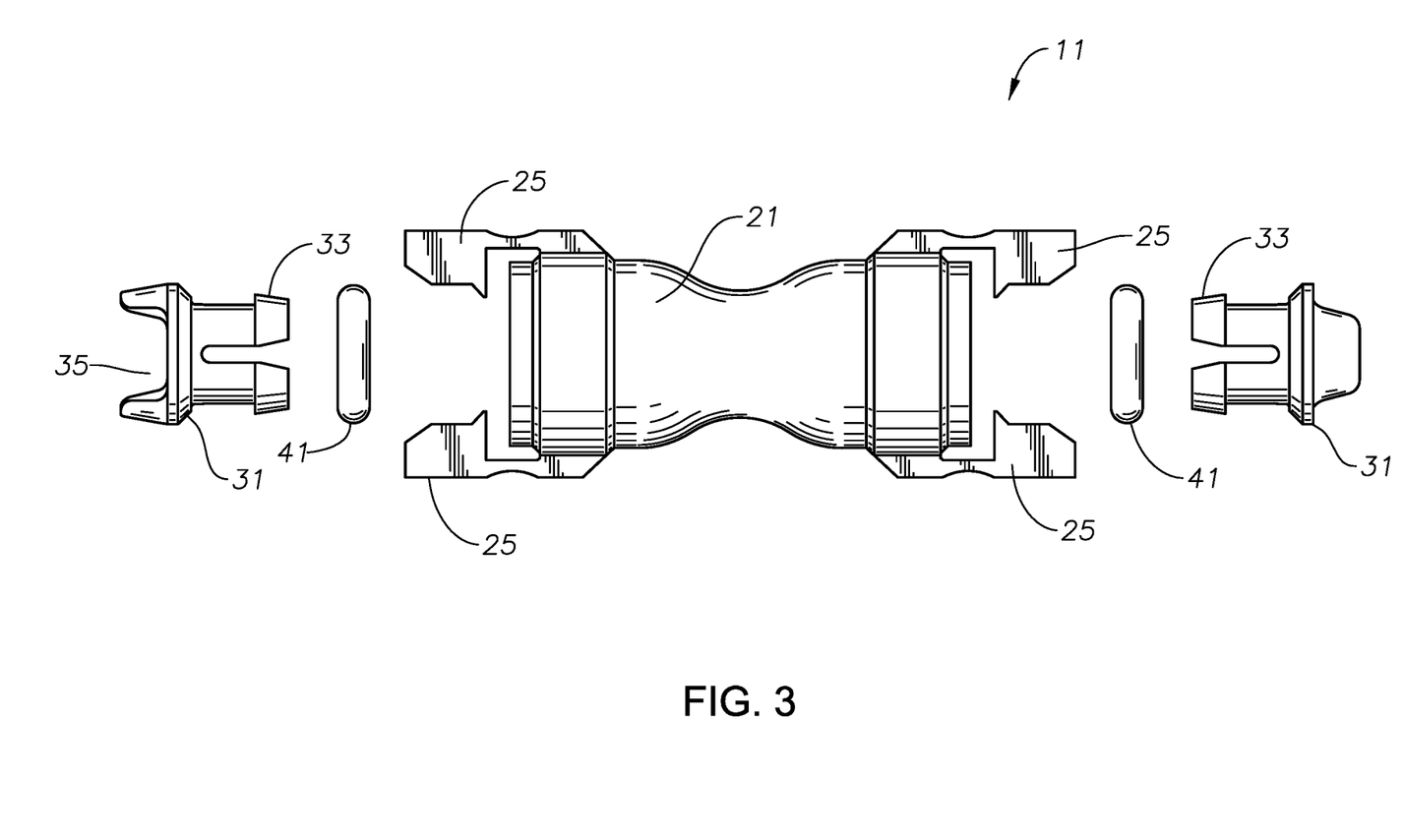
FIG. 3 is an enlarged exploded view of a connector in accordance with an embodiment of the present invention.
Figure 4:
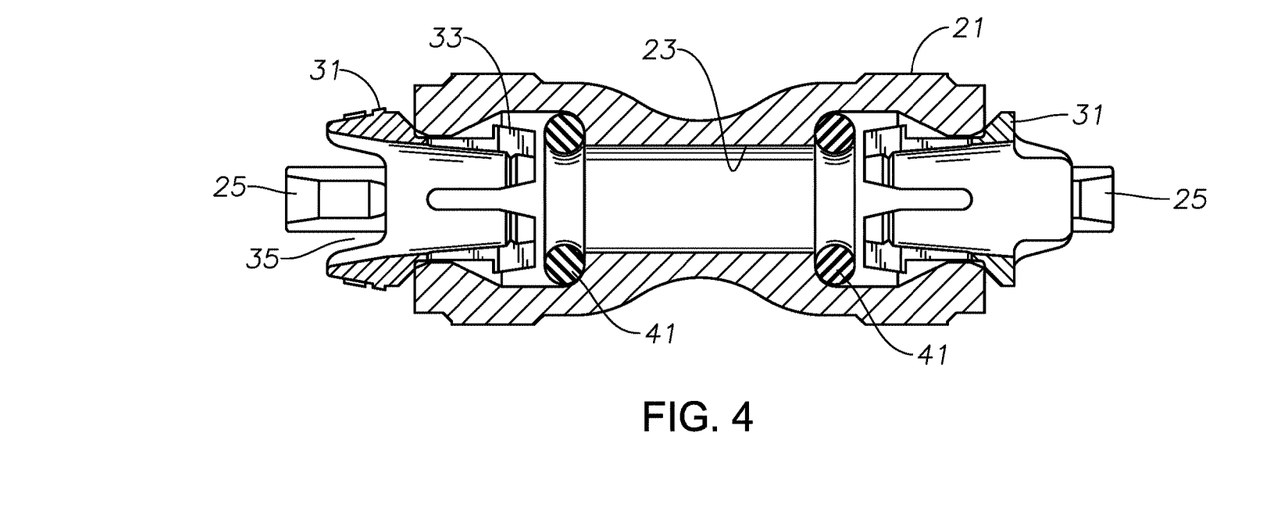
FIGS. 4 and 5 are longitudinal section views of the connector of FIG. 3, without tubing inserted, and with tubing inserted, respectively.
Figure 5:
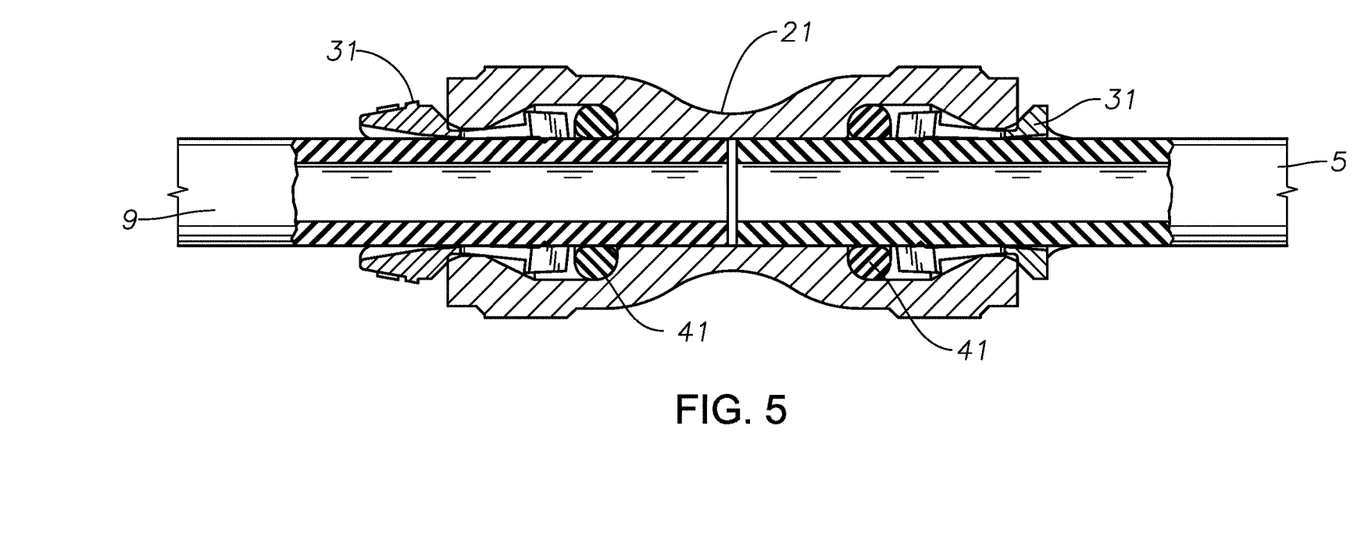

A collet 31 may be inserted or received in bore 23 at each end of body 21. Each collet 31 may be identical or similar and includes a plurality of flexible collet fingers 33 at one end, and an opposing end that projects outwardly or externally from body 21. Collets 31 may be at least temporarily retained in bore 23 by an outward radial projection on the ends of fingers 33, but are free to rotate within bore 23. A conical or tapered exterior surface tapers (from larger diameter to smaller) from the outward projection to approximately the center of collet 31. Collets 31 include an interior surface or bore that is dimensioned to receive a portion or length of tubing in the form of ends of extension tube 5 and feeding tube 9. Internal projections or "teeth" (a ring is illustrated) may be provided on the interior surface of collet fingers 33 to increase frictional engagement with the exterior of tubing inserted in collets 31. A locking notch 35 may be provided on the externally projecting portion of each collet 31.

As depicted in FIG. 5, upon insertion of tubing 5, 9 into bore 23 of body 21, collet fingers 33 of each collet 31 are deflected or displaced radially outwardly. An elastomer o-ring 41 may be provided in a recess in bore 23 adjacent each collet 31 and provides a fluid seal by engaging and exerting radial force on the exterior of the tubing within it.

Initially, tubing 5, 9 is retained within bore 23 of connector 21 only by frictional engagement between collet fingers 33 and the exterior of tubing 5, 9, and frictional force exerted by o-rings 41 on the exterior of tubing 5, 9. However, if collets 31 remain free to slide axially within bore 23, an attempt to withdraw tubing 5, 9 from bore 23 will slide collets 31 axially outwardly, along with tubing 5, 9. As collets 31 are withdrawn from bore 23 (along with or by the tubing), engagement between the tapered exterior of displaced collet fingers 33 and a corresponding interior surface of bore 23 (either the exterior of collets 31 or the interior of bore 23, or both surfaces, may be inclined or tapered) causes a radially inward force to be exerted by collet fingers 33 on the exterior of tubing 5, 9, increasing frictional engagement therebetween and resisting the withdrawal of tubing from bore 23. As withdrawal force on the tubing increases, so does the frictional engagement between collet fingers 33 and tubing 5, 9, resisting withdrawal of tubing from bore 23 of body 21.

Alternatively, if collets 31 are secured or locked against axially outward movement within and relative to bore 23 of body 21, then the initial state continues, in which the only force exerted on tubing 5, 9 is that of deflected collet fingers 33 and o-rings 41.

Figure 6:
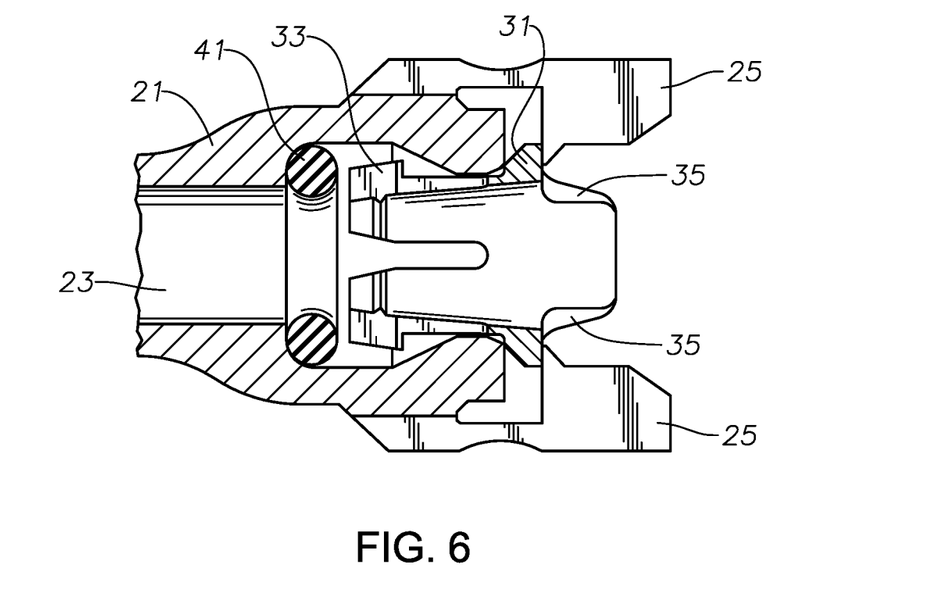
FIGS. 6 and 7 are enlarged views of a portion of the connector of FIG. 3.
Figure 7:
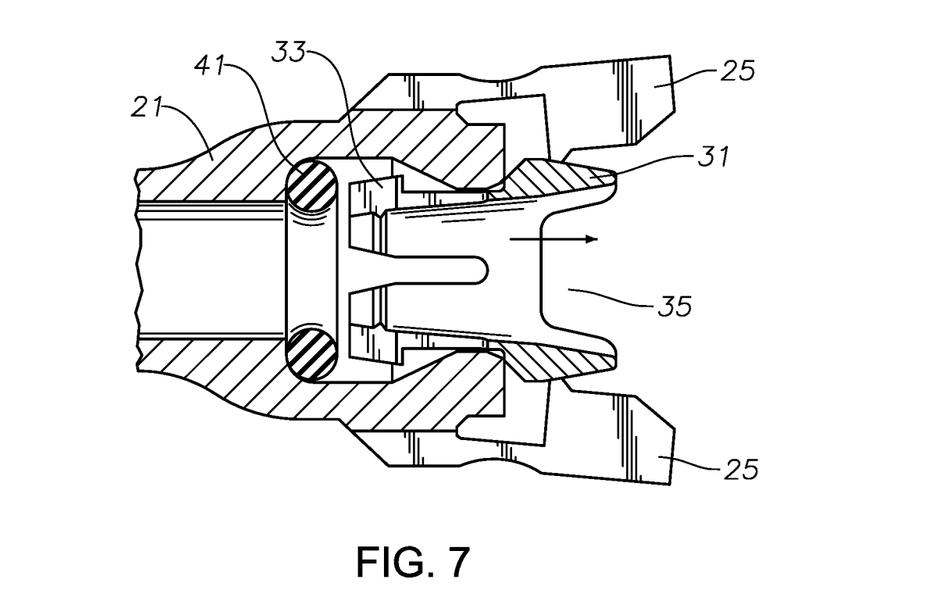

As illustrated in FIGS. 6 and 7, locking tabs 25 on body 21 and locking notch 35 on collet 31 may cooperate to provide a lock or locking mechanism or assembly with the ability to selectively secure collets against axial movement, or axial movement tending to withdraw collets 31 from bore 23 of body 21. In FIG. 6, collet 31 is rotated in bore 23 so that locking notches or recesses 35 are aligned or register with locking tabs 25 on body 21. This permits tabs 25 to move inwardly and engage with a surface at the bottom of each notch or recess 35. Thus, a collet 31 in this configuration or condition is prevented from moving axially outwardly from bore 23 and no additional radial force is generated by the action of collet fingers 33 on the exterior of tubing. This may be referred to as a "breakaway" or "quick-disconnect" mode. No user intervention is required, other than pulling on the tube, to separate the tube from the connector 11.

In FIG. 7, collet 31 is rotated 90 degrees from the position depicted in FIG. 6. In this position, notches or recesses 35 are no longer aligned with tabs 25 on body 21 and there is no engagement between notches 35 and tabs 25. Thus, collet 31 is thus free to move axially outwardly relative to bore 23 and body 21, permitting cooperation between the interior surface of bore 23 and collet fingers 33 to exert greater radial force on the exterior of the tubing and resisting its withdrawal from bore 23.

Thus, in the condition or configuration shown in FIG. 6, tubing is relatively easier to remove from bore 23 of connector 11 than in the condition shown in FIG. 7. In the embodiment illustrated in FIGS. 3 though 5, either end of connector 11 may be configured in the condition depicted in either FIG. 6 or FIG. 7.

The condition of FIG. 6, in which tubing is relatively easy to remove from body 21 of connector 11, is intended to provide the "breakaway" or "quick disconnect" feature: if excessive force or strain is exerted on tubing inserted in the connector 11, it will withdraw or "pull out" before damaging the feeding tube 9 or injuring patient 1, or both. The amount of force required to withdraw tubing in the configuration of FIG. 6 may be adjusted by the choice of material of collets 31, the degree of interference between the exterior of tubing and collet fingers 33 (and the presence, absence, or aggressiveness of any "teeth"), and the material and dimensions of o-rings 41.

The configuration of FIG. 7, on the other hand, is intended to provide a more traditional and robust tubing connection that is not easily disconnected until the collet 31 is placed in the configuration of FIG. 6.

Figure 8:
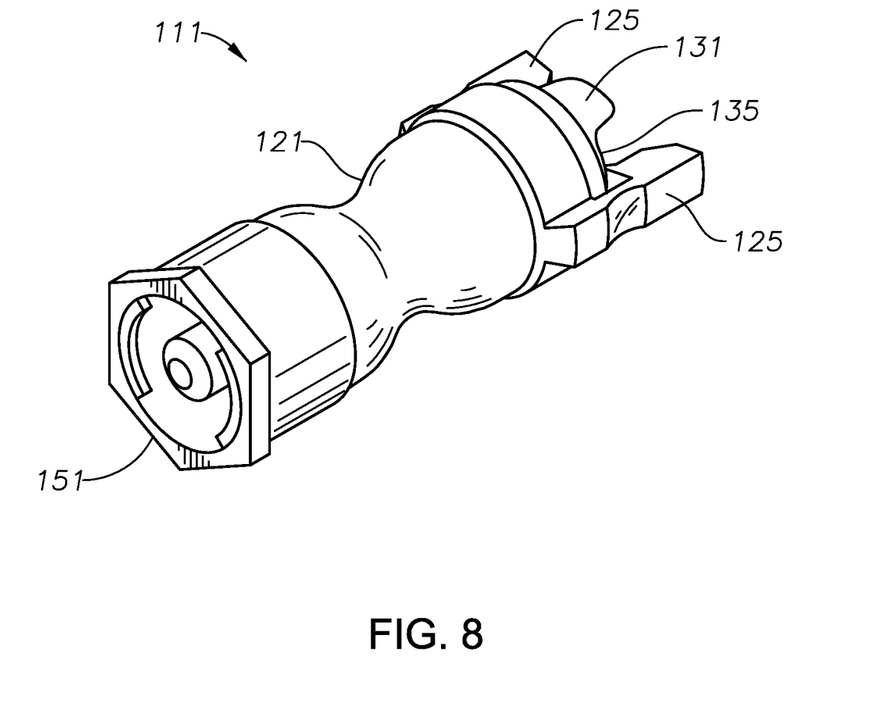
FIG. 8 is a perspective view of a connector in accordance with another embodiment of the present invention.

FIG. 8 illustrates an alternative embodiment of connector 111 in accordance with the present invention. In this embodiment, the collet, notch, and locking tab arrangement on one end of body 121 may be replaced by an entirely conventional tubing connection 151 of any description, leaving the functionality described above in connection with FIGS. 3 through 7 available on only one end of body 121. In FIG. 8, the illustrated conventional tubing connection 151 is a female EnFit® connector, while the opposing end of body 121 includes a collet 131, notches or recesses 135, and locking tabs 125 and is otherwise as described above in connection with FIGS. 1 through 7. Because EnFit® connector 151, and any other tubing connection has no breakaway or quick-disconnect feature, presumably the opposing end of connector 111 will be configured ordinarily in the condition of FIG. 6 to provide the breakaway feature at that end.

In operation, after feeding tube 9 is inserted into patient 1, connector 11, 111 may be installed onto the free end of feeding tube 9 by inserting the tubing into the end of body 21, 121. Either before or after insertion of tube 9, collet 31, 131 may be rotated to the desired configuration relative to locking tabs 25, 125 (the configuration of either FIG. 6 or FIG. 7). Extension or infusion tube 5 may then be connected to the other, opposing end of body 21 by a similar process (or by engaging its EnFit® or other tubing connector to the embodiment of FIG. 8). One or both ends of connector 11 may be set in the breakaway mode of FIG. 6. Less commonly, both ends of connector 11 may be set to the mode of FIG. 7, which causes connector to act in a more conventional fashion, requiring user intervention to separate it from either extension tube 5 or feeding tube 9.

The invention has been disclosed with reference to preferred and exemplary embodiments thereof. It is thus not limited, but is susceptible to variation and modification without departing from the scope and spirit of the invention.

We claim:

1. A connector for use in connecting a patient tube to a container of fluid, the connector comprising:
   a body;
   a bore extending through the body;
   a collet slidably disposed in the bore at a first end of the body, the collet dimensioned to receive and engage a first portion of tubing inserted into the collet, the collet configured to resist withdrawal of the tubing from the collet and the bore upon application of force to the tubing that moves the collet out of the bore;
   a user-actuable lock on the first end of the body, the user-actuable lock configured to selectively engage the collet and prevent movement of the collet outward relative to the body so that the collet does not resist withdrawal of the tubing from the bore;
   a tubing connection at a second, opposite end of the body, the tubing connection providing fluid communication between a second portion of tubing, the bore extending through the body, and the first portion of tubing inserted into the collet.

2. The connector of claim 1, further comprising an elastomer o-ring seal disposed in the bore adjacent the first end of the body, the o-ring dimensioned to engage and exert force on an exterior of the tubing upon insertion into the end of the body.

3. The connector of claim 2, wherein the first portion of tubing extends to the patient, and the second portion of tubing extends to the container of fluid.

4. The connector of claim 1, wherein the collet has an exterior surface that tapers along a length of the collet from a larger diameter to a smaller diameter.

5. The connector of claim 4, further comprising at least one internal projection on an interior surface of the collet.

6. The connector of claim 1, wherein the tubing connection is an enteral connector in compliance with ISO CD 80369-3.

7. The connector of claim 1, wherein the tubing connection further comprises:
   a second collet slidably disposed in the bore at the second end of the body, the collet dimensioned to receive and engage a portion of tubing inserted into the collet, the collet configured to resist withdrawal of the tubing from the collet and the bore upon application of force to the tubing that moves the collet out of the bore; and
   a second user-actuable lock on the second end of the body, the lock configured to engage the collet and prevent movement of the collet outward relative to the body so that the collet does not resist withdrawal of the tubing from the bore.

8. A connector for use in connecting a first portion of tubing connected to a patient and a second portion of tubing connected to a fluid reservoir, the connector comprising:
   a body having a pair of opposing ends;
   a bore extending through the body;
   a collet slidably disposed in the bore at each end of the body, each collet dimensioned to receive and engage a portion of tubing inserted into the collet, each collet configured to resist withdrawal of the tubing from the collet and bore upon application of force to the tubing that moves the collet out of the bore; and
   a user-actuable lock on each end of the body, the lock configured to selectively engage the collet and prevent movement of the collet outward relative to the body, so that the collet does not resist withdrawal of the tubing from the bore.

9. The connector of claim 8, further comprising an elastomer o-ring seal disposed in the bore adjacent each end of the body, each o-ring dimensioned to engage and exert force on an exterior of the tubing upon insertion into the end of the body.

10. The connector of claim 9, wherein the first portion of tubing leading to the patient is received in the bore at one end of the body, and the second portion of an extension tube leading to the fluid reservoir is received in the bore at an opposing end of the body.

11. The connector of claim 8, wherein each collet has an exterior surface that tapers along a length of the collet from a larger diameter to a smaller diameter.

12. The connector of claim 8, further comprising at least one internal projection on an interior surface of each collet.

13. A patient fluid apparatus comprising:
a fluid reservoir;
a first tube fluidly coupled to the fluid reservoir;
a second tube configured for connection to a patient; and
a connector fluidly connecting the first and second tubes, the connector including:
a body;
a bore extending through the body;
a collet slidably disposed in the bore at a first end of the body, the collet dimensioned to receive and engage a portion of one of the first and second feeding tubes inserted into the collet, the collet configured to resist withdrawal of the tube from the collet and the bore upon application of force to the tube that moves the collet out of the bore;
a user-actuable lock on the first end of the body, the user-actuable lock configured to selectively engage the collet and prevent movement of the collet relative to the body so that the collet does not resist withdrawal of the tube from the bore; and
a tubing connection at a second, opposite end of the body, the tubing connection providing fluid communication between another of the first and second tubes, the bore extending through the body, and the tube inserted into the collet.

14. The apparatus of claim 13, further comprising an elastomer o-ring seal disposed in the bore adjacent the first end of the body, the o-ring dimensioned to engage and exert force on an exterior of the patient tube upon insertion into the end of the body.

15. The apparatus of claim 13, wherein the collet further comprises:
an exterior surface that tapers along a length of the collet from a larger diameter to a smaller diameter; and
at least one internal projection on an interior surface of the collet.

16. The apparatus of claim 13, wherein the tubing connection is an enteral connector in compliance with ISO CD 80369-3.

17. The apparatus of claim 13, wherein the tubing connection further comprises:
a second collet slidably disposed in the bore at the second end of the body, the collet dimensioned to receive and engage a portion of tubing inserted into the collet, the collet configured to resist withdrawal of the tubing from the bore and body upon application of force to the tubing that moves the collet out of the bore; and
a second lock on the second end of the body, the lock configured to engage the collet and prevent movement of the collet outward relative to the body.

18. The apparatus of claim 13, wherein the user-actuable lock further comprises a pair of locking tabs carried on the body adjacent the collet, wherein the locking tabs selectively register and engage with corresponding notches formed in the collet to secure the collet against movement relative to the body and within the bore.

19. The connector of claim 1, wherein the user-actuable lock further comprises a pair of locking tabs carried on the body adjacent the collet, wherein the locking tabs selectively register and engage with corresponding notches formed in the collet to secure the collet against movement relative to the body and within the bore.

20. The connector of claim 8, wherein the user-actuable lock further comprises a pair of locking tabs carried on each end of the body adjacent the collet, wherein the locking tabs selectively register and engage with corresponding notches formed in the collet to secure the collet against movement relative to the body and within the bore.

\* \* \* \* \*